US008165908B2

(12) United States Patent
Bolle et al.

(10) Patent No.: US 8,165,908 B2
(45) Date of Patent: Apr. 24, 2012

(54) TOOL TIP WITH ADDITIONAL INFORMATION AND TASK-SENSITIVE DIRECT ACCESS HELP FOR A USER

(75) Inventors: Nikolaus Bolle, Baiersdorf (DE); Klaus-Michael Pauls, Hoechstadt (DE); Klaus Ullrich, Forchheim (DE); Bernhard Schild, Forchheim (DE); Michael Nofz, Erlangen (DE); Ute Feuerlein, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1593 days.

(21) Appl. No.: 11/192,550

(22) Filed: Jul. 29, 2005

(65) Prior Publication Data

US 2007/0027733 A1    Feb. 1, 2007

(51) Int. Cl.
*G06Q 10/00* (2012.01)
(52) U.S. Cl. .............. 705/7.27; 705/7.22; 705/7.38; 715/810; 715/839
(58) Field of Classification Search .................. None
See application file for complete search history.

(56) References Cited

U.S. PATENT DOCUMENTS

| | | | |
|---|---|---|---|
| 5,179,654 A | 1/1993 | Richards et al. | |
| 5,442,759 A | 8/1995 | Chiang | |
| 5,455,903 A * | 10/1995 | Jolissaint et al. | 715/835 |
| 5,999,911 A * | 12/1999 | Berg et al. | 705/7.26 |
| 6,078,325 A * | 6/2000 | Jolissaint et al. | 715/839 |
| 6,674,449 B1 * | 1/2004 | Banks et al. | 715/740 |
| 6,950,981 B2 * | 9/2005 | Duffy et al. | 715/222 |
| 7,020,844 B2 * | 3/2006 | Trevino et al. | 715/772 |
| 7,133,833 B1 * | 11/2006 | Chone et al. | 705/7.27 |
| 7,567,360 B2 * | 7/2009 | Takahashi et al. | 358/1.15 |
| 7,657,868 B2 * | 2/2010 | Shenfield et al. | 717/107 |
| 2002/0152244 A1 * | 10/2002 | Dean et al. | 707/530 |
| 2003/0095144 A1 * | 5/2003 | Trevino et al. | 345/764 |

(Continued)

FOREIGN PATENT DOCUMENTS

DE    38 52 034 T2    5/1995

OTHER PUBLICATIONS

Jane Fedorowicz, Ulric J Gelinas Jr, Catherine Usoff, & George Hachey. (2004). Twelve Tips for Successfully Integrating Enterprise Systems Across the Curriculum. Journal of Information Systems Education, 15(3), 235-244.*

(Continued)

*Primary Examiner* — Lynda Jasmin
*Assistant Examiner* — Gurkanwaljit Singh
(74) *Attorney, Agent, or Firm* — Lempia Summerfield Katz LLC

(57) ABSTRACT

An interactive software application provides workflow assistance related to the proper performance of work steps in the workflow. The workflow assistance may include step by step instructions detailing the proper operation of the user interface to complete the current work step. Additionally, the workflow assistance may include a virtual simulation demonstrating the proper operation of the user interface to complete the work step. Alternate workflow assistance may be provided for alternate manners of completing the work step. The software application also may initiate the performance of a work step via a primary operation on an icon associated with the work step. Workflow assistance associated with the work step may be presented via a secondary operation performed on the icon. Workflow assistance also may be directly accessible from the user interface or from a help menu superimposed upon other images displayed on the user interface.

11 Claims, 12 Drawing Sheets

U.S. PATENT DOCUMENTS

| | | | |
|---|---|---|---|
| 2003/0095150 A1* | 5/2003 | Trevino et al. | 345/810 |
| 2003/0149599 A1* | 8/2003 | Goodall et al. | 705/2 |
| 2003/0171947 A1* | 9/2003 | Ledford et al. | 705/1 |
| 2003/0179245 A1* | 9/2003 | Akagi | 345/804 |
| 2003/0212580 A1* | 11/2003 | Shen | 705/2 |
| 2004/0190057 A1* | 9/2004 | Takahashi et al. | 358/1.15 |
| 2005/0027733 A1* | 2/2005 | Donahue | 707/102 |
| 2005/0193340 A1* | 9/2005 | Amburgey et al. | 715/709 |
| 2005/0240428 A1* | 10/2005 | Gabrick et al. | 705/1 |
| 2006/0059423 A1* | 3/2006 | Lehmann et al. | 715/530 |

OTHER PUBLICATIONS

German Office Action dated Aug. 23, 2007 and English translation.

* cited by examiner

800

802 → Where is Help?
804 →     Open & Close
806 →     Move & Scale

808 → Help Content
810 →     Workflow Structure
812 →     Information Levels
814 →     Previous & Next Step 816 → Synchronized Help
818 →     Workflow Help 820 → Help Features
822 →     Show Me (Animation)
824 →     Error Management
826 →     Comment
828 →     Index & Search
830 →     History Function

FIGURE 8

TOOL TIP WITH ADDITIONAL INFORMATION AND TASK-SENSITIVE DIRECT ACCESS HELP FOR A USER

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies: Copyright © 2005, Siemens, All Rights Reserved.

BACKGROUND

Interactive computer software applications assist users of the application in the performance of various procedures to which the applications are directed, e.g. word processing, accounting, etc. For example, interactive software applications may be directed toward medical applications such as facilitating the evaluation of internal bodily images obtained using a medical imaging process, such as ultrasound, X-ray or magnetic resonance imaging technologies. Such software applications may be directed toward other types of applications as well, both medical and non-medical.

Given their complexities, conventional interactive software applications may require a voluminous amount of associated documentation to educate, train and/or assist the user in understanding and applying the functions of the application. Typically, such documentation is provided to the customer via hard copy, such as user manuals, binders, application guides, hardware manuals, and other booklets. The documentation also may be provided by various electronic media, such as stored in an electronic file and accessible via an online help function.

However, users may find it difficult to locate data, i.e. specific subject matter or a specific topic, pertaining to a desired topic using the provided documentation. For instance, the desired topic may relate to the operation of the software, the features and capabilities of the software, educational topics, or other training topics. Further, if the user does successfully locate the desired data, this data may fail to solve the user's problem or fail to answer unanticipated questions, such as questions that develop as the user utilizes the software application. In addition, where multiple sources of documentation are provided, these sources may present inconsistent data, thereby detracting from the overall usefulness of the software application.

BRIEF DESCRIPTION OF THE DRAWINGS

FIG. 8 illustrates an exemplary help menu for providing information related to the operation of the user interface according to one embodiment;

DETAILED DESCRIPTION

Figure 1:
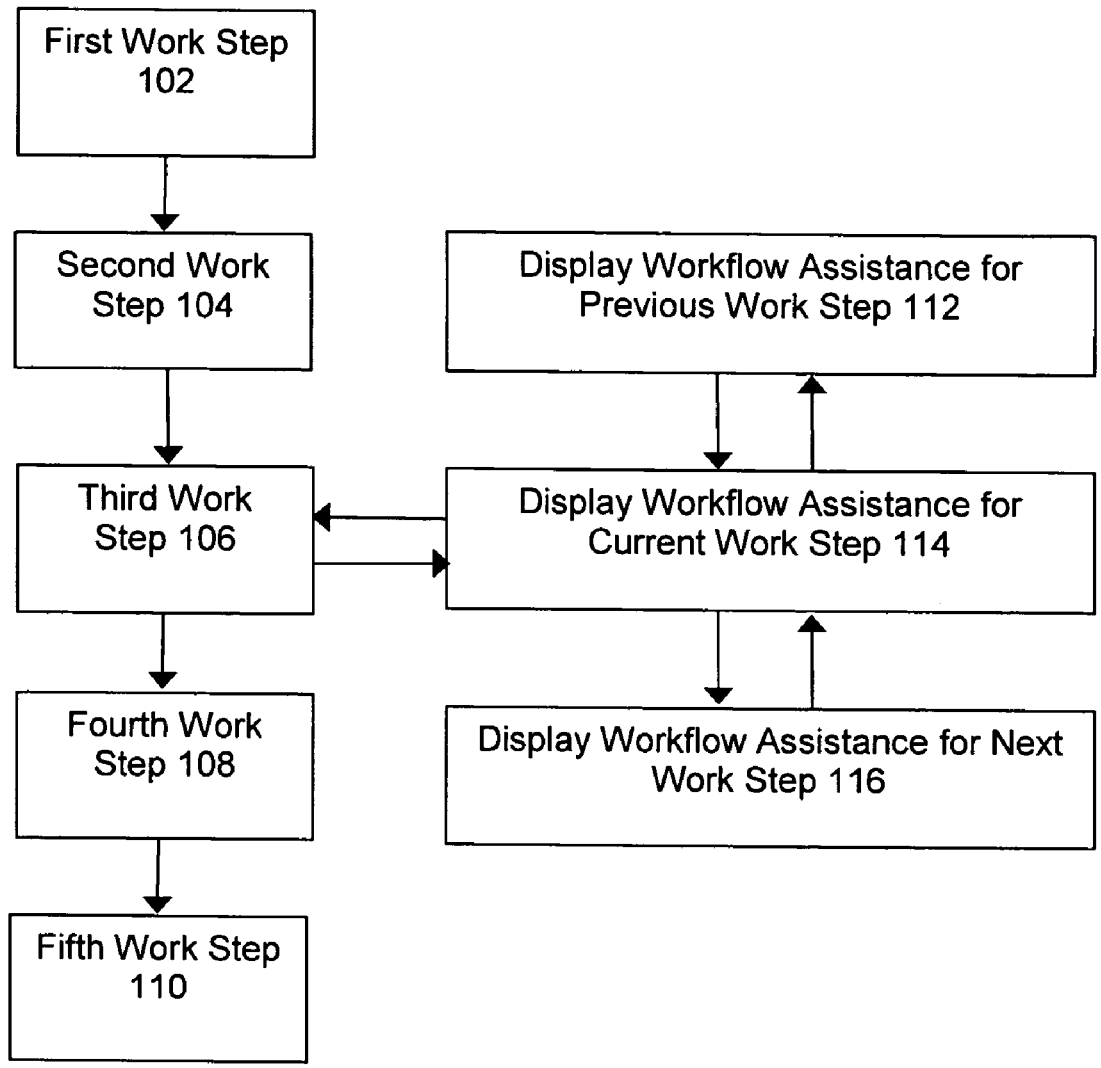
FIG. 1 illustrates an exemplary flow chart for providing workflow assistance on a user interface according to one embodiment.

The disclosed embodiments relate generally to interactive software applications that assist a user with one or more workflows. More particularly, the disclosed embodiments relate to an interactive software application that presents workflow assistance for the one or more workflows.

An interactive software application provides workflow assistance to a user. The software application may assist the performance of a workflow and track the work steps within the workflow. If a user has questions that arise while performing the workflow, the software application may present workflow assistance in an efficient manner. While the disclosed embodiments will be described with respect to a single workflow, it will be appreciated that multiple independent or inter-related workflows may be supported.

The workflow assistance may include step by step instructions detailing the proper operation of a user interface to complete a work step in the workflow. These instructions may be presented in a textual or graphical format, or a combination thereof. The workflow assistance also may include a virtual simulation, such as a graphic animation or video, demonstrating the proper operation of the user interface to complete the work step. The workflow assistance may further include alternate step by step textual/graphical instructions or an alternate virtual simulation detailing an alternate proper operation of the user interface to complete the work step.

The software application may track user's progress through the work steps of the workflow such that upon being queried by the user for workflow assistance, workflow assistance related to the current work step is quickly provided. Workflow assistance related to the current work step may be directly accessed via a single operation performed on the user interface regardless of the work step that is to be performed next. Alternatively, the workflow assistance may be accessed from a help menu, or other interface construct, superimposed upon other images related to the current work step displayed on the user interface.

The software application may present a number of icons or other user-interactive graphic elements on a user interface that each correspond to an individual work step, or group of work steps, in the workflow. The performance of a work step may be initiated via a primary interactive operation on the icon corresponding to that work step, such as clicking on the icon using a mouse or other pointing/user interface device coupled with the computer executing the application. In practice, however, an inexperienced user may first desire information and instructions related to the corresponding work step prior to initiating that particular work step. To accommodate such requirements, workflow assistance associated with the work step may be presented by performing a secondary operation on the icon associated with the work step, such as positioning a cursor over the icon with the mouse, without any further actions, e.g. without pressing any buttons on the mouse. In this way, the workflow assistance associated with the particular work step may be accessed via the icon corresponding to the work step prior to initiating that work step.

The initiation of a work step by an inexperienced user may create problems in some situations. For example, in certain instances, the completion of a work step may be time sensitive and any delay in the completion of the work step after initiation may have ramifications, serious or otherwise, such as with a medical procedure in which delay may be life threatening, expose the patient to additional risk or simply inconvenience the patient or others who are waiting. Accordingly, as will be described below in more detail, the icon corresponding to the work step represents a convenient and efficient tool by which an inexperienced user may access workflow assistance related to the work step to expedite initiation and completion of the work step.

In one embodiment, the performance of the secondary operation on the icon presents information and instructions related to the corresponding work step directly in response to the performance of the secondary operation, such as by displaying a pop up window or other interface element. Alternatively, the performance of the secondary operation on the icon may present information and instructions related to the corresponding work step indirectly, such as by displaying an another interactive graphical element, such as a button or other interface element, the subsequent actuation of which causes the display of the requisite subject matter, e.g. pop up or other display. For instance, the secondary operation on the icon may directly result in a functional identifier, such as a graphical balloon having short functional description therein, that explains the function of the corresponding work step to be displayed on the user interface. The workflow assistance associated with the particular work step also may be accessed either directly or indirectly from the functional identifier. For example, an operation performed on the functional identifier, such as a selection using the mouse, may result in an additional display being rendered on the user interface containing a functional explanation that further explains the work step. An additional operation performed on the functional explanation may further result in additional, or more detailed, workflow assistance associated with the work step to be displayed on the user interface.

FIG. 1 illustrates an exemplary flow chart 100 for providing workflow assistance on a user interface. In the example of FIG. 1, the workflow includes a first work step 102, a second work step 104, a third work step 106, a fourth work step 108, and a fifth work step 110. The workflow may have additional, fewer, or alternate work steps.

The user interface assists a user to complete the work steps in the workflow. At each work step 102, 104, 106, 108, 110, a user may develop questions related to the current work step, the previous work step, the next work step, other work steps, or the workflow in general. Upon receiving a query from a user for workflow assistance, the user interface of the present embodiment presents workflow assistance. The workflow assistance may include information and instructions related to the proper operation of the user interface to complete the current work step, other work steps, or the workflow. Additional, fewer, and alternate types of workflow assistance may be presented on the user interface.

As shown by the example in FIG. 1, at the third work step 106 in the workflow, the user may query the system for workflow assistance regarding the current or third work step 106. In response to the query for workflow assistance, the user interface displays workflow assistance for the current work step 114. After which, the user may perform the current work step or query for the system for workflow assistance regarding the previous or next work step. In response to a query for workflow assistance regarding the previous or next work step, the user interface displays workflow assistance for the previous or next work step 112, 116, respectively. Subsequently, the user may continue to access workflow assistance regarding each additional previous or next work step in the workflow.

The workflow assistance displayed for the previous, current, and next work steps 112, 114, 116 may include textual instructions, graphical instructions, or combinations thereof, detailing the proper operation of the user interface to complete the previous, current, and next work steps 112, 114, 116, respectively. The instructions may provide step by step guidance to a user regarding the proper performance of the work step. By following the step by step guidance, a user may properly complete the work step.

Alternatively, or in addition to, the textual/graphical instructions, the workflow assistance displayed for the previous, current, and next work steps 112, 114, 116 may include a virtual simulation demonstrating the proper operation of the user interface to complete the previous, current, and next work steps 112, 114, 116, respectively. The virtual simulation may provide guidance in the form of an animation, video or digital movie illustrating the operations needed to be performed on the user interface to complete the work step. By following or mimicking the guidance provided by the virtual simulation, the user may properly complete the work step.

The virtual simulation may be presented in a dedicated pop-up window. The virtual simulation may include illustrating the movement of a cursor on the user interface. The virtual simulation may demonstrate the operation of the user interface by moving an icon representing a cursor over various other icons, buttons, menus, or other items displayed on the screen associated with the work step, using either a virtual representation of the actual user's screen or the actual screen itself. As the cursor moves over each item on the display, the virtual simulation may show the result of performing an operation of that item, i.e., the virtual simulation may demonstrate what a user should expect the user interface to display in response to an operation performed on an item associated with the work step. The virtual simulation may include textual or graphical messages or indicators to highlight certain aspects of the work step or the operation of the user interface.

The virtual simulation may illustrate moving a mouse on the user interface to demonstrate the proper operation of the user interface. The virtual simulation may include demonstrating a specific operation on an item displayed on the user interface, such as an icon, button, or menu, associated with the work step, such as indicating that a user is to left or right click upon the item using the mouse.

The virtual simulation may include demonstrating operations performed on the user interface via alternate input devices, such as keyboards, haptic devices, haptic screens, touch pads, touch screens, joysticks, controllers, or other input devices. The virtual simulation may include additional, fewer, or alternate demonstrations of the proper operation of the user interface The virtual simulation also may provide audio step by step instructions and/or other information along with the visual presentation. The virtual simulation may request that the user operate an input device and subsequently provide haptic feedback to the user in response to the user's actions and regarding the proper operation of the user interface. The virtual simulation may include rotating objects such that a three dimensional depiction of the work step is displayed. The virtual simulation may step the user through performing the actual work step. Alternate forms of virtual simulations may be used.

Upon reaching a work step in the workflow, the user may have a choice as to the manner in which the work step is to be performed. For instance, the work step may be completed by more than one proper operation of the user interface. Hence, the workflow assistance may include alternate instructions regarding the proper operation of the user interface to complete the work step. The alternate instructions may include textual/graphical instructions or a virtual simulation.

Figure 2:
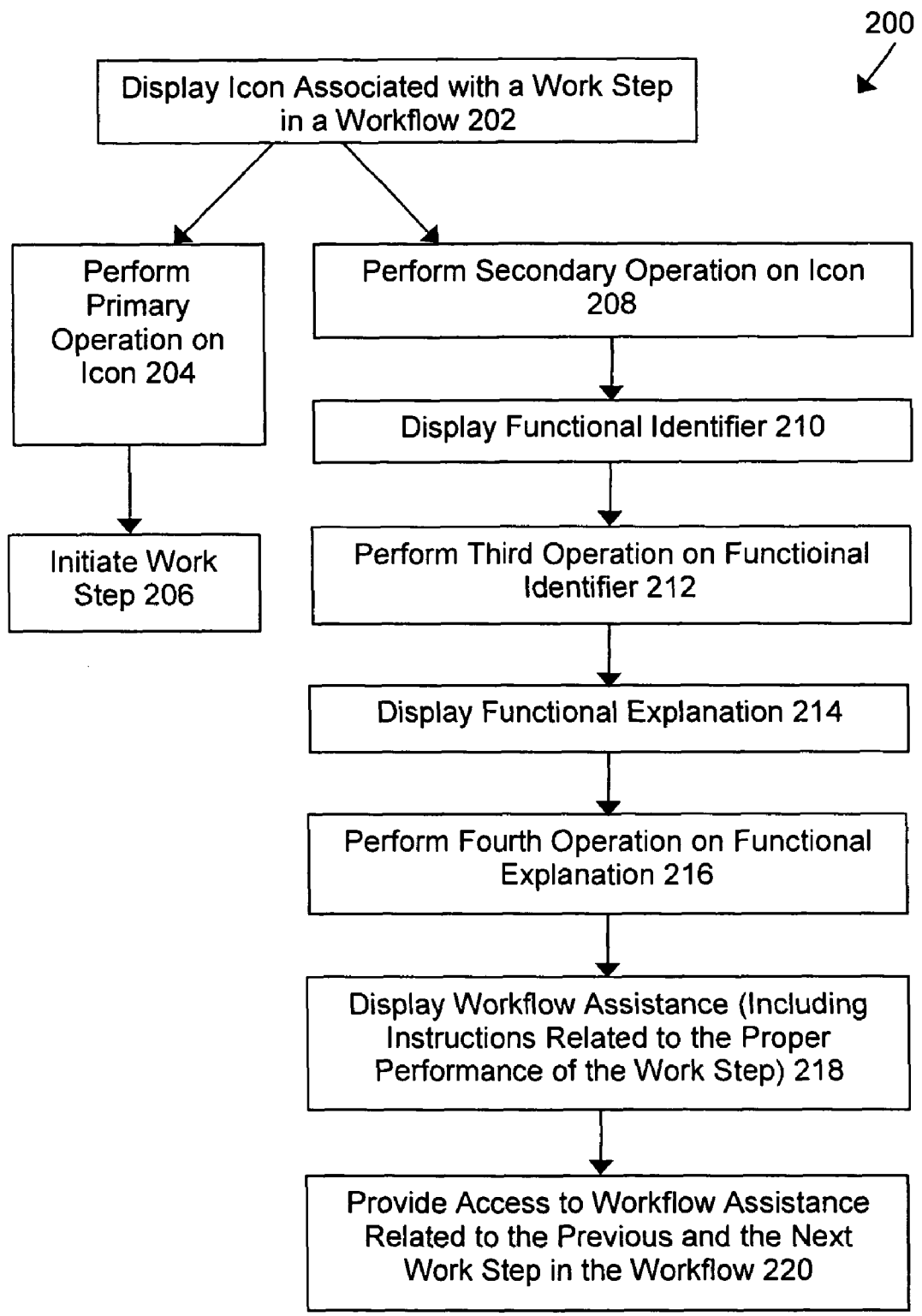
FIG. 2 illustrates an exemplary flow chart for accessing workflow assistance via a user interface according to one embodiment.

FIG. 2 illustrates an exemplary flow chart 200 for one method of accessing workflow assistance via a user interface. The method may include displaying an icon associated with a work step in a workflow 202 on a user interface. A performance of a primary operation on the icon associated with the work step 204 may initiate the work step 206. The primary operation may include moving a cursor over the icon via an input device and selecting the icon. The cursor may be moved over the icon via a mouse, keyboard, haptic device, haptic screen, touch screen, touch pad, joystick, controller, or other input device. The icon may be selected by pressing a button on the input device, such as by actuating the left mouse button, i.e. left clicking, on a mouse, touching the button on a touch screen, or pressing the enter key on a keyboard. Alternate primary operations on the icon associated with the work step may be used.

In some situations, a user may not desire to initially initiate the work step 206, but would rather first receive workflow assistance regarding the work step associated with the icon for various reasons. For example, the proper performance of a work step after initiation may be time sensitive. In one embodiment, the work step may be related to a medical procedure that involves exposing a patient to radiation during the work step. Additionally, it may be more efficient to receive work flow assistance before commencing an unfamiliar work step, other wise a user may have to halt the performance of a work step midstream and wait until workflow assistance is obtained.

A performance of a secondary operation on the icon associated with the work step 208 may display an associated functional identifier 210. The functional identifier is a brief identification of the function of the work step, typically two or three words in length. By displaying the functional identifier on the user interface, a user may determine if additional information regarding the work step is desired. The functional identifier may be an icon or a box containing the short textual identification. Alternate functional identifiers may be used, such as an audible indication.

The secondary operation may be performed via the same input device that performed the primary operation. For instance, the secondary operation may be performed by merely moving the cursor with the mouse over the icon. In this manner, the secondary operation on the icon may be performed with out performing the primary operation on the icon.

Alternatively, the secondary operation may be performed by right clicking on the mouse after the cursor has been moved over the icon. Additionally, the secondary operation may be performed via a different input device than the input device used to perform the primary operation. For instance, either the first or secondary operation may be performed by touching the icon displayed on a touch screen. Alternate secondary operations on the icon associated with the work step may be used.

A user may desire additional information regarding the work step associated with the icon. A performance of a third operation on the functional identifier 212 may display a functional explanation 214 on the user interface. In one embodiment, the third operation includes moving the cursor over the functional identifier and clicking upon the functional identifier with the mouse. Alternate third operations may be used.

The functional explanation explains the work step in further detail than the functional identifier. The functional explanation may be typically two to three sentences in length. By displaying the functional explanation on the user interface, a user may determine if additional workflow assistance regarding the work step is desired. The functional explanation may be displayed in a window, an icon, or a box containing the textual/graphical explanation. Alternate functional explanations may be used.

If workflow assistance regarding a work step is desired, a performance of a fourth operation on the functional explanation 216 may display the workflow assistance regarding the work step 218. The workflow assistance may include the step by step textual instructions detailing the proper operation of the user interface and the virtual simulation demonstrating the proper operation of the user interface discussed above. In one embodiment, the functional explanation is displayed in a dedicated pop-up window that includes a button and the fourth operation includes moving the cursor over the button and clicking upon the button via a mouse.

After the workflow assistance is displayed for a work step, a user may access the workflow assistance regarding a previous or next work step in the workflow 220. The method of accessing the workflow assistance may include additional, fewer, or alternate work steps.

The input device that performs the third and fourth operations may be a mouse, keyboard, haptic device, haptic screen, touch pad, touch screen, joystick, controller, or other input device. However, alternate methods of accessing the workflow assistance may not include either or both the third and fourth operations. Accordingly, the workflow assistance regarding a work step may be directly or indirectly accessed via a secondary operation performed on an icon associated with the work step, the primary operation performed on the icon being operable to initiate the performance of the work step.

Figure 3:
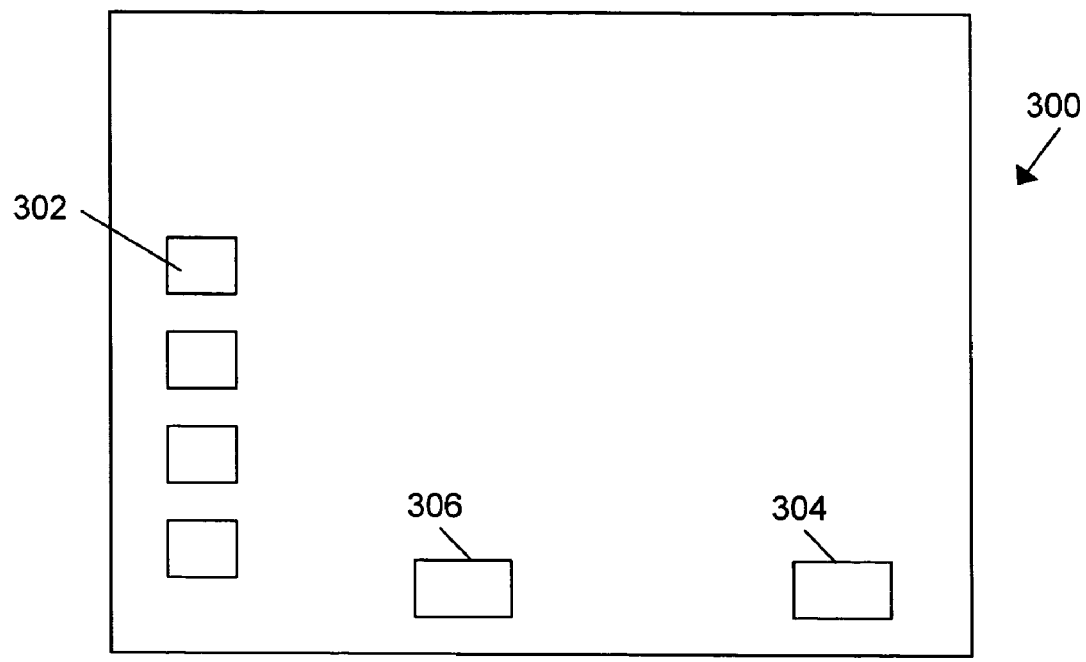
FIG. 3 illustrates an exemplary user interface displaying icons related to work steps in a workflow according to one embodiment.

FIG. 3 is an exemplary user interface 300. The user interface 300 displays icons corresponding to individual work steps 302, a help button 304, and a tutorial button 306. The user interface 300 may display additional, fewer, or alternative items.

A workflow may have a plurality of work steps, each work step having an associated icon 302. The user interface may assist in the performance of a workflow. The user interface may guide the user through a series of work steps in the workflow. However, at any point in the workflow, questions may arise regarding the workflow or the proper performance of a work step. Rather than providing a conventional database search engine to type in questions or provide a list of answers to frequently asked questions, the system may track or monitor the performance of the work steps and identify the current work step. As a result, if the user queries for workflow assistance, workflow assistance specifically tailored to the current work step may be quickly provided. For instance, a user may query for workflow assistance regarding the current work step via the help button 304. The help button 304 may always be displayed on the user interface regardless of the current work step. A single operation performed on the globally accessible help button 304 may provide direct access to workflow assistance regarding the current work step.

In other words, the user interface 300 may assist the performance of each work step in a workflow. The work area of the user interface 300 may change according to the work step being performed. However, the help button 304 always provides direct access to workflow assistance regarding the current work step. Accordingly, the inconvenience and time spent navigating a search engine to locate the pertinent or desired workflow assistance regarding a current work step may be alleviated.

A help menu may be accessed via the tutorial button 306. An operation performed on the tutorial button 306 may result in the help menu being superimposed upon other images displayed on the user interface 300. The help menu may present a list of categories regarding the operation of the user interface about which a user may have questions. The help menu also may provide access to workflow assistance regarding the current work step. By superimposing the help menu over other images displayed on the user interface 300, the user may able to continue view images required to be seen to complete the current work step while having more direct and convenient access to workflow assistance. In one embodiment, the help menu is superimposed over images obtained from a medical imaging process.

Figure 4:
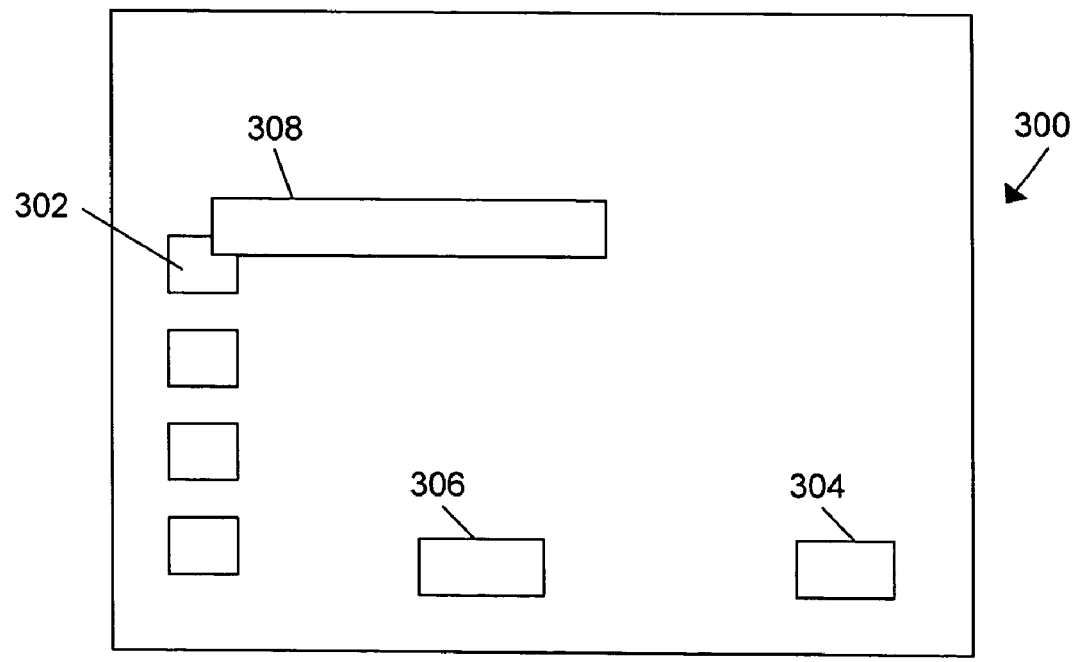
FIG. 4 illustrates an exemplary user interface displaying a functional identifier associated with one work step according to the embodiment of FIG. 3.

FIG. 4 is another exemplary user interface 300. The user interface displays a number of icons 302, each icon corresponding to an individual work step. A primary operation performed on each icon 302 may initiate the corresponding work step. A secondary operation performed on each icon 302 may generate a functional identifier 308 on the user interface that identifies the work step associated with the icon 302. The primary and secondary operations may include the operations discussed above.

For instance, the primary operation may include moving a cursor over the icon 302 via a mouse and subsequently left clicking on the mouse to initiate the work step. The secondary operation may include only moving a cursor over or into the vicinity of the icon 302 via an input device. The secondary operation does not initiate the work step. Alternate primary and secondary operations may be used, including those discussed herein.

Figure 5:
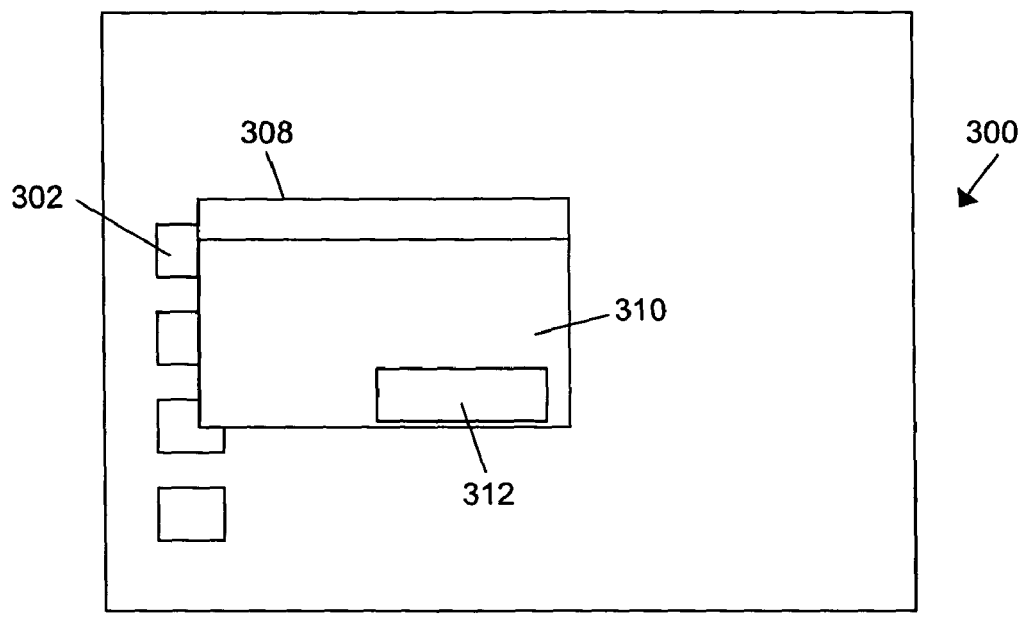
FIG. 5 illustrates an exemplary user interface displaying a functional explanation associated with the work step according to the embodiment of FIG. 3.

FIG. 5 is another exemplary user interface 300. The user interface displays an icon 302 corresponding to a work step, a functional identifier 308 that identifies the work step, a functional explanation 310 that explains the work step, and a button 312 for accessing workflow assistance regarding the work step. The user interface may include additional, fewer, or alternate items.

The functional explanation 310 may be accessed via an operation performed on the functional identifier 308. The operation performed on the functional identifier 308 may be an operation as discussed above. For instance, a cursor may be moved over the functional identifier 308 via a mouse to access the functional explanation 310. A user also may be required to click on the functional identifier 308 to access the functional explanation 310. Or a user may touch the functional identifier 308 if displayed on a touch screen. Alternative operations may be performed on the functional identifier 308 to access the functional explanation 310.

The functional explanation 310 may be displayed in a pop-up window with text and/or graphics explaining the function of the work step. The pop-up window may include a button 312 for accessing workflow assistance regarding the work step. Alternate functional explanations may be used.

An operation performed on the functional explanation 310 may access workflow assistance regarding the work step. The operation may include the operations previously discussed. For instance, a cursor may be moved over the button 312 and clicked upon via a mouse to access the workflow assistance regarding the work step. Or a user may touch the button 312 or the functional explanation 310 if displayed on a touch screen. Alternate operations to access the workflow assistance may be used. For example, the operation may include clicking upon or touching a functional explanation that does not have a button dedicated to accessing workflow assistance.

Figure 6:
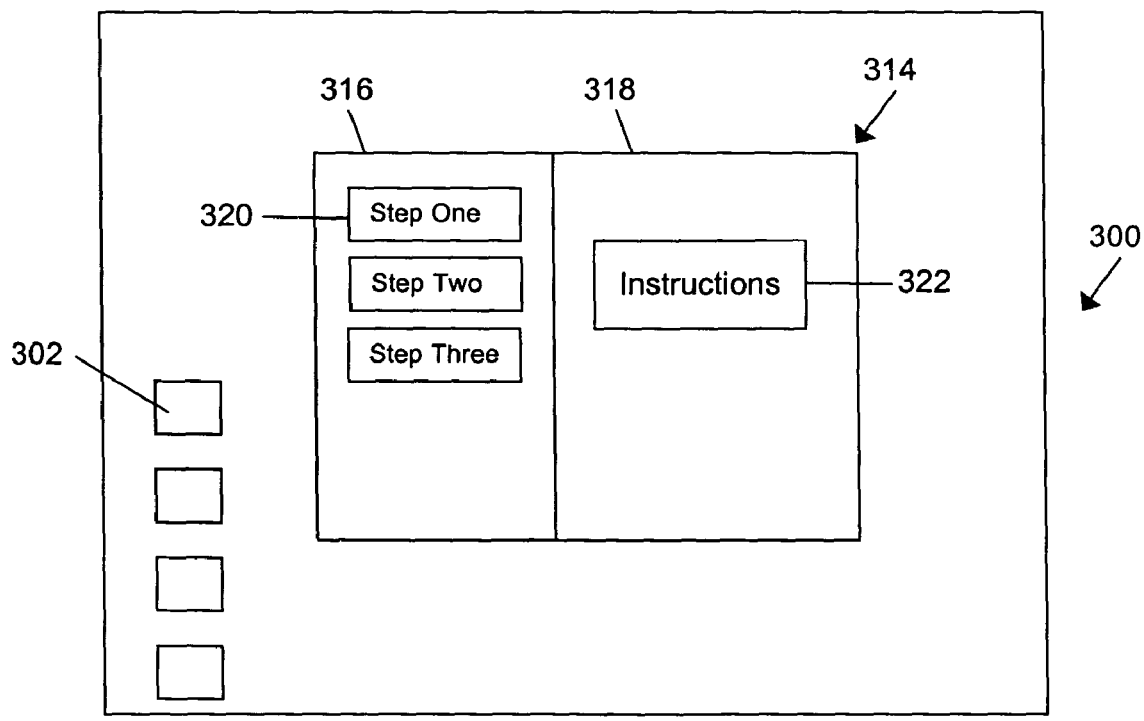
FIG. 6 illustrates an exemplary user interface displaying workflow assistance associated with the work step according to the embodiment of FIG. 3.

FIG. 6 is another exemplary user interface 300. The user interface 300 displays workflow assistance 314 accessed by performing an operation on the functional explanation. The workflow assistance 314 may include displaying a workflow list 316 and workflow information 318. The workflow assistance 314 may include additional, fewer, or alternate items.

The workflow list 316 may list the work steps 320 in the workflow. The user interface may distinguish the current work step from the other work steps 320 in the workflow list 316. The workflow list 316 may include additional, fewer, or alternate items.

The workflow information 318 may include workflow assistance as described herein. The workflow information 318 may include instructions 322 for the proper operation of the user interface to complete a work step. For example, the instructions 322 may include step by step textual information detailing, or a virtual simulation demonstrating, the proper operation of the user interface to complete the work step. The instructions 322 may include alternate instructions regarding an alternate proper operation of the user interface to complete the work step. Additional, fewer, or alternate instructions may be provided.

The workflow assistance 314 may include the capability of accepting and saving user specific comments pertaining to each work step. The workflow assistance 314 also may include general information regarding the work step or workflow. The workflow assistance 314 may provide a search engine to search a database based upon user specified queries. Alternate workflow assistance may be provided.

Figure 7:
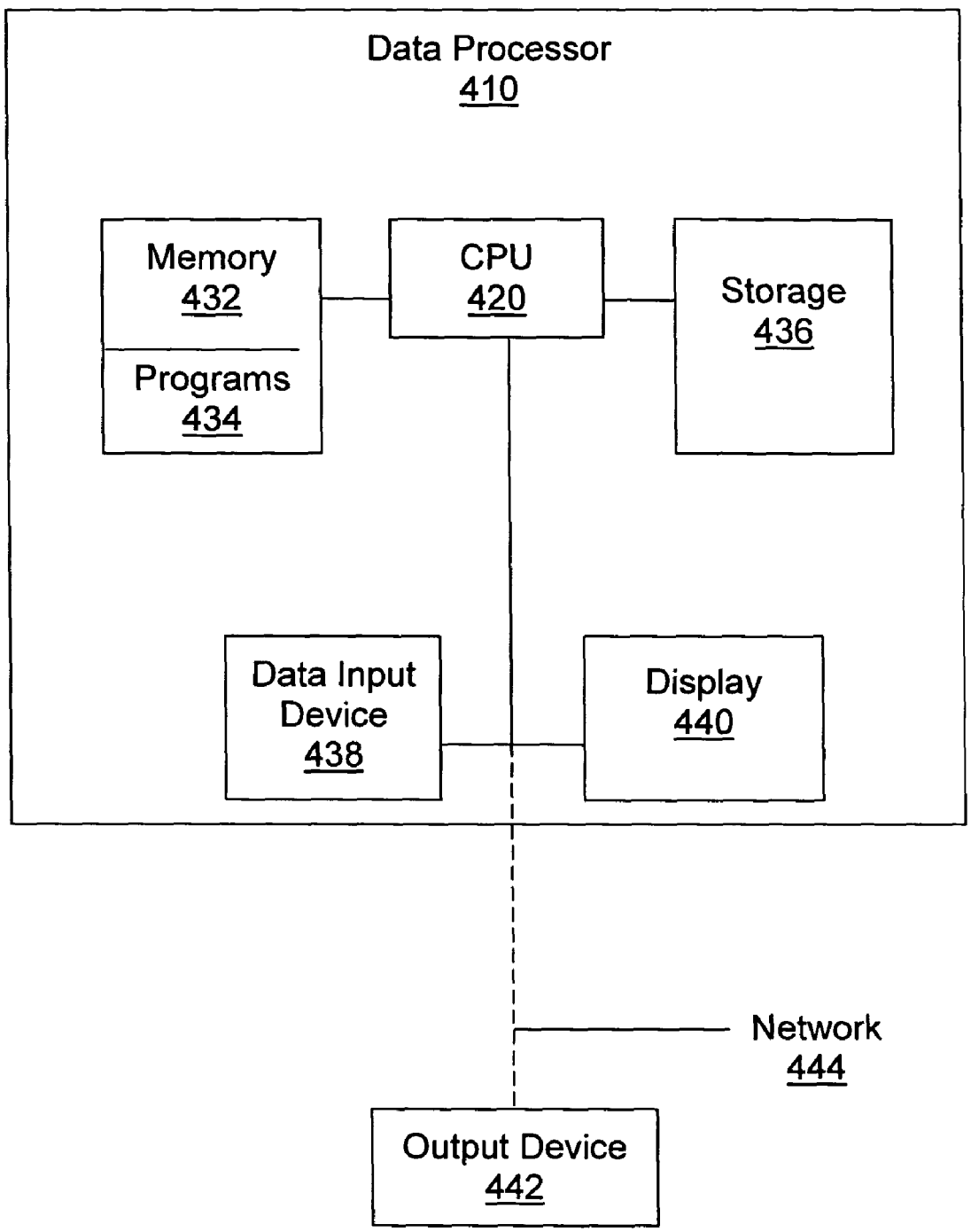
FIG. 7 illustrates an exemplary data processor configured or adapted to provide workflow assistance according to one embodiment.

FIG. 7 illustrates an exemplary data processor 410 configured or adapted to provide workflow assistance to a user. The data processor 410 may include a central processing unit (CPU) 420, a memory 432, a storage device 436, a data input device 438, and a display 440. The processor 410 also may have an external output device 442, which may be a display, a monitor, a printer or a communications port. The processor 410 may be coupled with a user interface for presenting information and receiving instructions and/or user requests via the display 440, the external output device 438, or other display. Herein, the phrase "coupled with" is defined to mean directly connected to or indirectly connected through one or more intermediate components. Such intermediate components may include both hardware and software based components. The processor 410 may be a personal computer, work station, picture archiving and communication system (PACS) station, or other medical imaging system. The processor 410 may be interconnected to a network 444, such as an intranet, the Internet, or an intranet connected to the Internet. The data processor 410 may be interconnected to a network 444. The data processor 410 is provided for descriptive purposes and is not intended to limit the scope of the present system. The data processor 410 may have additional, fewer, or alternate components.

A program 434 may reside on the memory 432 and include one or more sequences of executable code or coded instructions that are executed by the CPU 420. The program 434 may be loaded into the memory 432 from the storage device 436. The CPU 420 may execute one or more sequences of instructions of the program 434 to process data. Data may be input to the data processor 410 with the data input device 438 and/or received from the network 444. The program 434 may interface the data input device 438 and/or the network 444 for the input of data. Data processed by the data processor 410 may be provided as an output to the display 440, the external output device 442, the network 444, and/or stored in a database. The program 434 and other data may be stored on or read from machine-readable medium, including secondary storage devices such as hard disks, floppy disks, CD-ROMS, and DVDs; electromagnetic signals; or other forms of machine readable medium, either currently known or later developed.

The data processor 410 provides workflow assistance to a user. The data processor 410 may run a software application or program 434 that performs a number of operations or work steps in a workflow related to a specific procedure. The data processor 410 may track the performance of the work steps in the workflow of the procedure.

During the performance of each work step in the workflow, a user may develop one or more questions. Using the data input device 438 or other input device, the user may query the data processor 410 for information related to the question or questions. Upon receipt of a user request for information, the data processor 410 may present information on the display 440, output device 442, or other output device that answers the user's question or provides information pertaining to the user specified topic.

The data processor 410 may present training information that instructs the user on the features and capabilities of the software application or program 434. The training information may be presented on the display 440, output device 442, or other output device. The training information may instruct the user on the proper operation of the software application during each work step of a workflow. For example, as a user progresses through the work steps of a workflow using the software application, a user may arrive at an unfamiliar work step or a work step that the user does not know how to properly complete. The software application may quickly provide guidance to the user on how to complete the work step. In one embodiment, the software application provides animated instructions that graphically depict the proper operation of the software application's user interface for a given work step.

The work step for which the software application presents guidance information may be the current work step in the workflow. However, the software application may permit a user to access guidance and other information pertaining to any work step regardless of the current work step. In other words, the guidance and/or other information for each work step is globally accessible from any point in the software application or the workflow. Additionally, the user may access guidance or other information for the previous or next work step in the workflow.

The data processor 410 may present of a workflow structure on the display 440, output device 442, or other display device. For example, the data processor 410 may display a list of work steps in the workflow on a display screen. The current work step or a user-selected work step about which information is desired may be distinguished from the other work steps in the workflow.

The data processor 410 may present additional information levels on the display 440, output device 442, or other display device. The additional information levels may present information regarding each work step in addition to step by step instructions to complete the work step. Alternatively, the additional information levels may present step by step instructions to complete an alternate workflow or work step. Other additional information may be presented.

The data processor 410 may provide error management. The data processor 410 may monitor the performance of the current work step. If an error is detected in the performance of the current work step, the data processor 410 may display an error message indicating to the user that a problem exists on the display 440, output device 442, or other output device 442. The data processor 410 also may generate an error message suggesting remedial action to be taken by a user.

At each work step in the workflow, the data processor 410 may permit a user to enter and save comments regarding the work step. The comments may be saved in the memory 432, the storage 436, or other memory unit. The data processor 410 may retrieve the comments for use during subsequent procedures. Additionally, the data processor 410 may generate and save a report regarding each work flow. The report may include the user entered comments. The reports may be saved in the memory 432, the storage 436, or other memory unit and subsequently retrieved by the data processor 410.

The data processor 410 may provide the capability to search a database of information stored in the memory 432, the storage 436, or other storage unit. The data processor 410 may provide a search engine that searches based upon user entered queries. Alternatively, the data processor 410 may present an alphabetical index or a table of contents by which the database may be searched. The database may include procedural information, such as information pertaining to a work step, workflow, procedure, or other information.

Exemplary Embodiment for Medical Software Applications

In one embodiment, the software application provides workflow assistance for a medical procedure. The medical procedure may involve the analysis of internal bodily images obtained from a medical imaging process and the evaluation of a region of interest. The medical software application may access a database containing detailed information related to medical procedures, illnesses, bodily organs, and other medical subjects. The medical software application may present educational and training information that is organized and searchable by organ, medical procedure, type of illness, or other medical topic. The medical procedures may relate to pre-examination, examination, and post-examination medical procedures.

The medical software applications may be used on data processors 410 located at hospitals, clinics, or other medical facilities. The users of the software applications may include doctors, nurses, and other medical personnel. The software applications may assist the medical personnel with the diagnosis of medical conditions and the treatment of patients.

Various screen displays which present options to the user and receive selections from the user may be utilized to implement this functionality. The user interface may be accessed on a locally available media such as a local hard disk or CD-ROM or may be located on a network server and accessed via a known uniform resource locator ("URL") or other method of network access. In one embodiment, links are provided to a software program called Syngo™, developed by Siemens AG, located in Erlangen, Germany. Syngo™ is a software package used in conjunction with medical imaging systems manufactured by Siemens to provide a simplified and unified operational interface to a heterogeneous mix of medical imaging equipment.

Syngo™ consists of two parts: the first part includes user features related to systems operation, and the second part addresses service personnel needs (troubleshooting the systems, running system tests, setting up remote access, etc.). The medical software applications may be accessed/run through a hyperlink provided in the Syngo™ service software. For example, an adaptive performance system CD-ROM may be inserted into the system's CD drive, or may be otherwise available, such as by a remote connection to a corporate intranet or the Internet.

The software applications may relate to processing images illustrating an enhanced region of interest within a patient. For example, various types of contrast medium may be administered to a medical patient. The contrast mediums enhance the scans acquired by scanning a patient or images of the patient, the scans and images may be recorded by an external recording device as enhancement data. The contrast medium typically travels through a portion of the body, such as in the blood stream, and reaches an area that medical personnel are interested in analyzing. While the contrast medium is traveling through or collected within a region of interest, a series of scans or images of the region of interest of the patient may be recorded for processing and display by the software applications. The enhanced region of interest may show the brain, the abdomen, the heart, the liver, a lung, a breast, the head, a limb or any other body area.

The expected enhancement data may be generated for one or more specific type of image processes that are used to produce the images or scans of the patient. In general, the types of imaging processes that may be used to produce patient images or scans of internal regions of interest include radiography, angioplasty, computerized tomography, ultrasound and magnetic resonance imaging (MRI). Additional types of imaging processes that may be used include perfusion and diffusion weighted MRI, cardiac computed tomography, computerized axial tomographic scan, electron-beam computed tomography, radionuclide imaging, radionuclide angiography, single photon emission computed tomography (SPECT), cardiac positron emission tomography (PET), digital cardiac angiography (DSA), and digital subtraction angiography (DSA). Alternate imaging processes may be used.

FIG. 8 illustrates an exemplary help menu 800 for providing information related to the operation of the user interface. The help menu 800 may be accessed via a tutorial button located on the user interface. The help menu 800 may be superimposed over internal bodily images obtained from a medical imaging process so as to permit the continued evaluation of the internal bodily images while permitting direct access to workflow assistance via the help menu 800. Workflow assistance may be accessed by a single operation performed on the help menu 800.

The help menu 800 may provide access to workflow assistance in the form a list of topics on which a user may desire information or provide access to step by step textual instructions or a virtual simulation regarding the proper operation of the user interface to complete a work step. In the example shown, the help menu 800 provides workflow assistance regarding "Where is Help" 802, "Open & Close" 804, "Move & Scale" 806, "Help Content" 808, "Workflow Structure" 810, "Information Levels" 812, "Previous & Next Step" 814, "Synchronized Help" 816, "Workflow Help" 818, "Help Features" 820, "Show Me (Animation)" 822, "Error Management" 824, "Comment" 826, "Index & Search" 828, and "History Function" 830 topics. Additional, fewer, or alternate topics may be used.

Each topic may illustrate the proper operation of the user interface with respect to that topic. For example, the "Show Me (Animation)" 822 topic may present a virtual simulation showing the proper operation of the user interface to complete to a work step. The "Error Management" 824 topic may illustrate an error message identifying an error in the performance of a work step, as well as recommended remedial action. The "Comment" 826 topic may illustrate how to properly enter notes pertaining to an individual work step.

Figure 9:
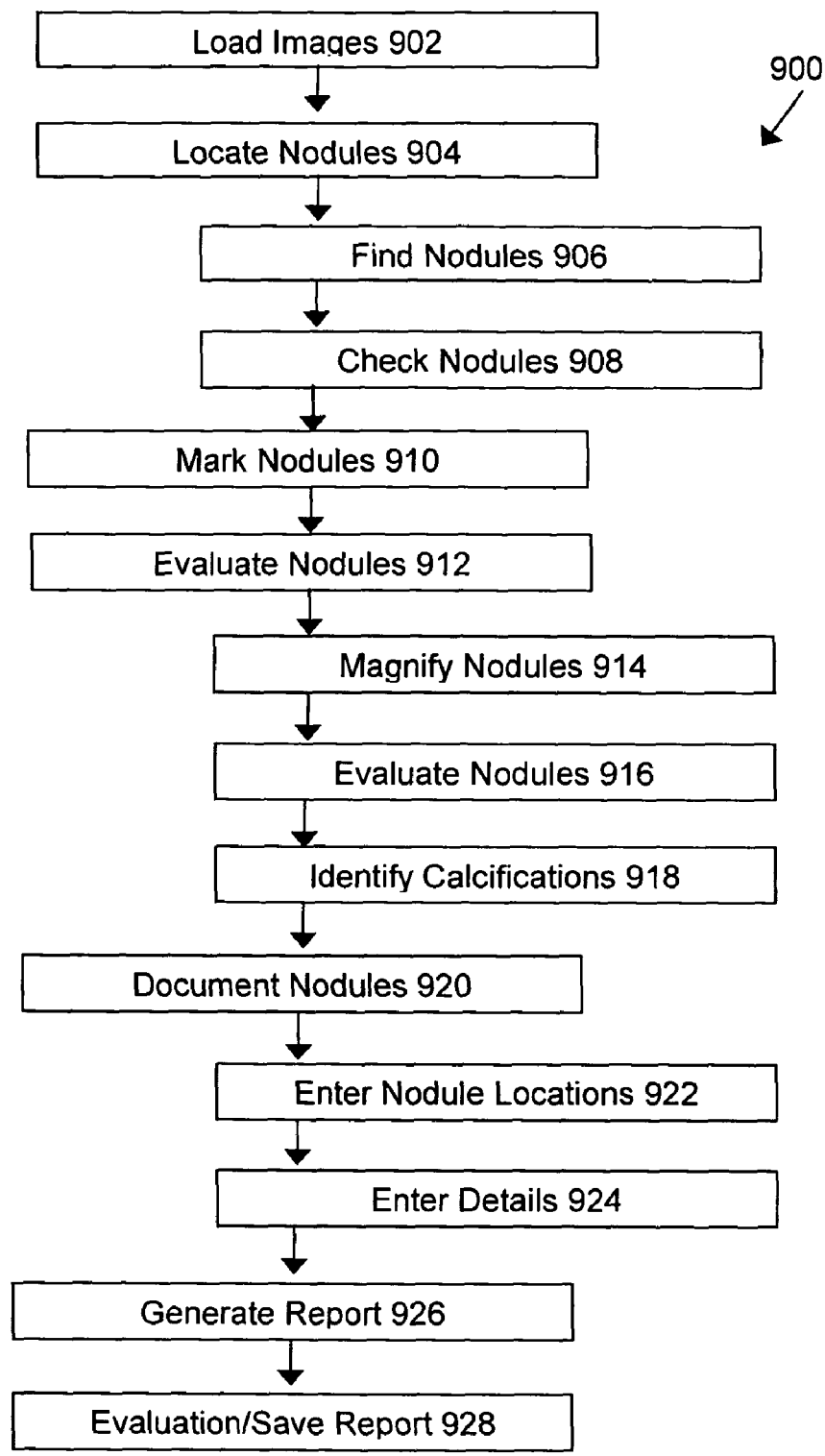
FIG. 9 illustrates an exemplary workflow.

FIG. 9 illustrates an exemplary workflow 900 for a medical procedure involving the analysis of images obtained from a medical imaging process and the evaluation of a region of interest. The workflow 900 includes a plurality of work steps and a number of work steps may have sub-work steps. For the example shown, the workflow 900 includes the load images 902, locate nodules 904, mark nodules 910, evaluate nodules 912, document nodules 920, generate report 926, and evaluate/save report 928 work steps.

The locate nodules 904 work step includes the find nodules 906 and check nodules 908 sub-work steps. The evaluate nodules 912 work step includes the magnify nodules 914, evaluate nodules 916, and identify calcifications 918 sub-work steps. The document nodules 920 work step includes the enter nodule locations 922 and enter details 924 sub-work steps. The exemplary workflow 900 may include additional, fewer, or alternate work steps and sub-work steps.

For the example shown, the objective of the medical procedure is to display and evaluate lung nodules or tumors. Alternate bodily parts also may be evaluated. The user is permitted to choose a single examination or a follow-up study. The single evaluation is directed toward an initial evaluation of a data record and/or continuation of a first evaluation. The follow-up study is used to compare existing examinations. Changes in the size of nodules in internal bodily images may be computed and displayed graphically.

Figure 10:
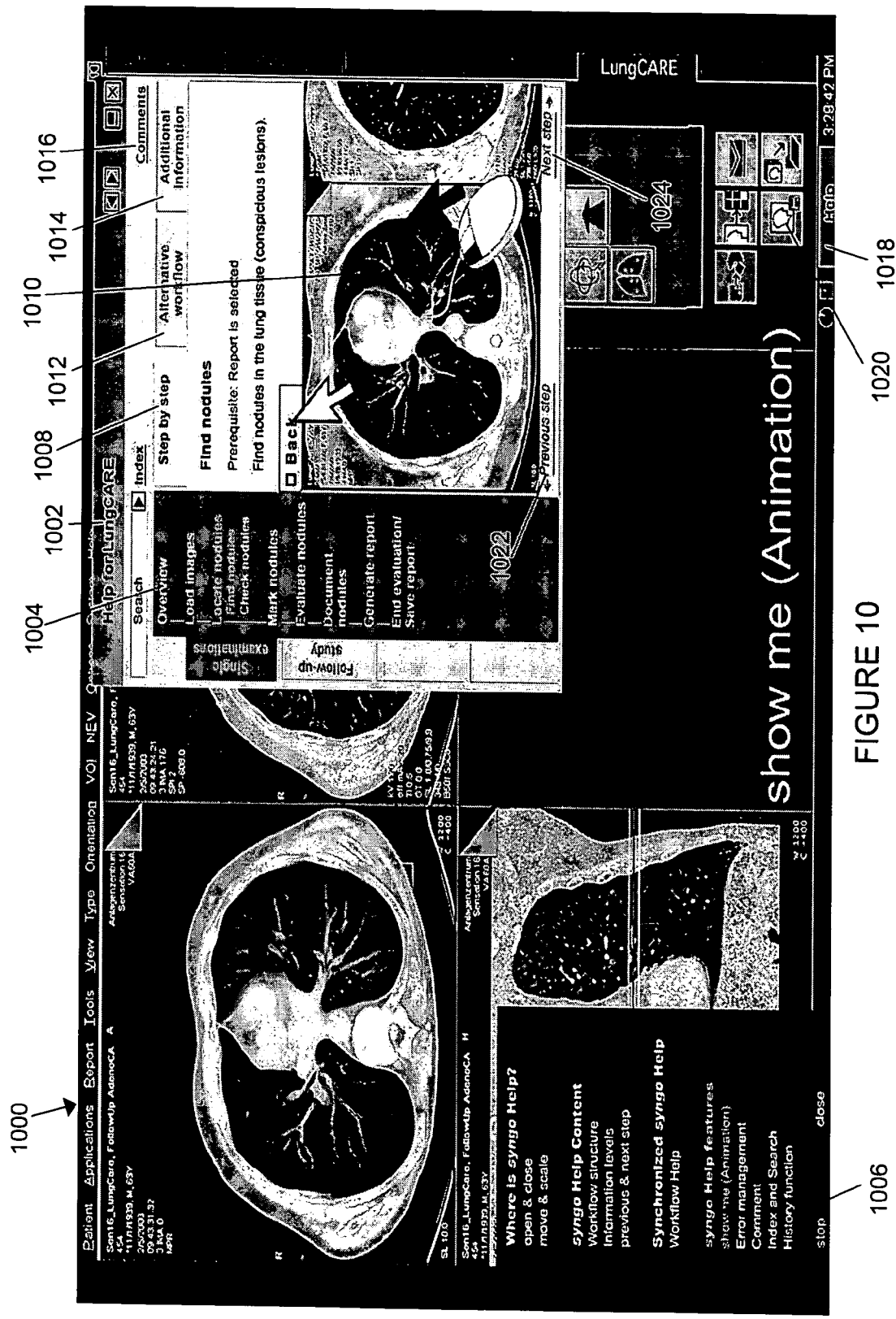
FIG. 10 illustrates exemplary workflow assistance for a workflow assisted by a user interface according to one embodiment.

FIG. 10 illustrates exemplary workflow assistance 1002 for a workflow assisted by a user interface 1000. The workflow assistance 1002 shown includes displaying a list of the work steps 1004. The work steps displayed include the following: (1) load images, (2) locate nodules, (3) mark nodules, (4) evaluate nodules, (5) document nodules, (6) generate report, and (7) end evaluation/save report. Additional, fewer, or alternate work steps may be included in the exemplary workflow. The current work step in the workflow may be distinguished on the display screen from the other work steps.

The workflow assistance 1002 may be accessed via a help menu 1006. An operation performed on the user interface, such as clicking upon a button or touching a touch screen, may result in the help menu 1006 being superimposed over other images displayed on the user interface. The help menu 1006 may be globally accessible to a user regardless of the point in the workflow that the user is currently at.

The help menu 1006 permits a user to access workflow assistance that includes step by step instructions 1008 on how to properly complete a work step or a sub-work step. The step by step instructions 1008 may be presented as text, graphic images or combinations thereof. The step by step instructions 1008 also may be presented as a virtual simulation 1010 demonstrating the proper operation of the user interface to complete the work step. As shown, the virtual simulation

1024 may be an animation illustrated the proper movement and operation of an input device, such as a mouse, to complete the work step.

The workflow assistance 1002 also may include alternate instructions 1012 regarding an alternate operation of the user interface to complete the work step. The alternate instructions 1012 may be presented as step by step textual and/or graphical instructions or as a virtual simulation. Additional, fewer, or alternate instructions may be presented.

The workflow assistance 1002 may include presenting additional information 1014 regarding the work step. The additional information 1014 may be information related to the work step other than instructions regarding the proper performance of the work step.

The workflow assistance 1002 may provide a comments button 1016. An operation performed on the comments button 1016 may permit a user to enter and save comments and notes associated with the work step.

Alternatively, the workflow assistance 1002 related to a work step may be accessed by either a help button 1018 or an icon 1020. The help button 1018 may provide direct access to workflow assistance for the current work step via a single operation on the help button 1018. The icon 1020 may provide indirect access to the workflow assistance regarding the work step associated with the icon via the performance of a secondary operation on the icon, as discussed herein.

The workflow assistance 1002 may provide a previous step icon 1022 and a next step icon 1024. The previous step icon 1022 may permit the user to access information regarding the previous work step in the workflow, including workflow assistance. The next step icon 1024 may permit the user to access information regarding the next work step in the workflow, including workflow assistance.

Figure 11:
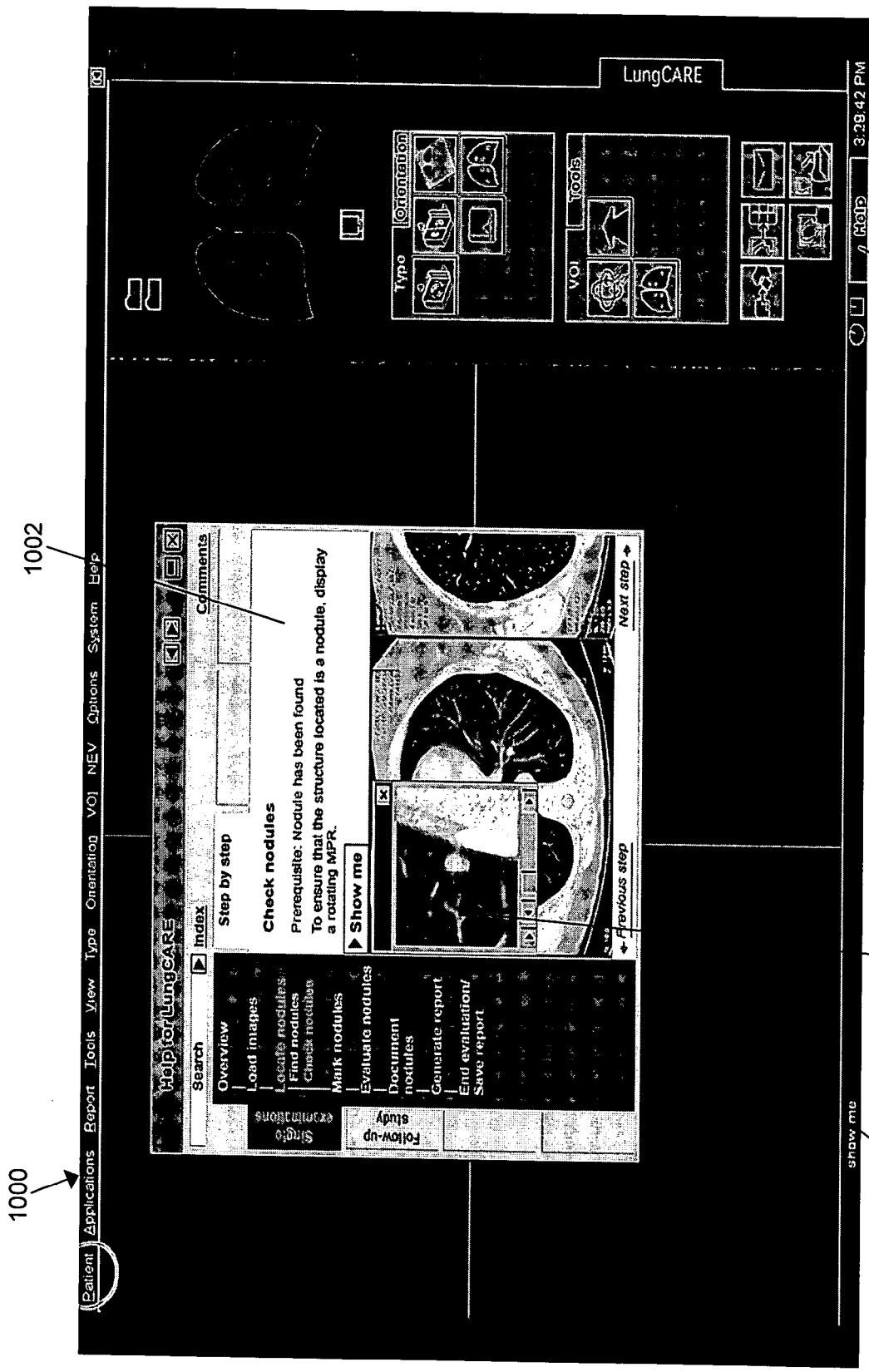
FIG. 11 illustrates another exemplary workflow assistance for a workflow assisted by a user interface according to one embodiment.

FIG. 11 illustrates exemplary workflow assistance 1002 for a workflow of a medical procedure assisted by a user interface 1000. The example of FIG. 11 illustrates the check nodule sub-work step that is directed toward ensuring that the structure located is a nodule or a tumor. The workflow assistance 1002 displays a virtual simulation 2024, which in the example shown is a video, of rotating images to facilitate verification that the structure located within a medical image is a nodule or a tumor, as opposed to a vessel or other image. The rotation of the images provides a three-dimensional view of images that enhances the evaluation of possible nodules and tumors. The virtual simulation 1024 demonstrates the completion of the work step and may be displayed on the user interface in a pop-up window.

The workflow assistance 1002 shown in FIG. 11 may be directly accessed via the help button 1018. An operation on the help button 1018 may result in workflow assistance 1002 regarding the current work step in the workflow to be displayed. Alternatively, the workflow assistance may be accessed via an icon 1020 associated with the work step. A secondary operation performed on the icon 1020 may result in workflow assistance 1002 regarding the current work step in the workflow to be displayed. Or the workflow assistance may be accessed via a help menu superimposed upon the user interface. The help menu may be access via the "show me" tutorial button 1026.

In general, as shown in FIG. 11, the exemplary workflow includes the mark nodule work step that permits a user to draw a marker around the located nodule and establish a volume of interest to be evaluated. Subsequently, the evaluate nodules work step may be performed. The evaluate nodules work step may include three sub-work steps: magnify nodules, evaluate nodules, and identify calcifications. The magnify nodules sub-work step may magnify or rotate a nodule on the display screen to facilitate a more detailed evaluation of the nodule. The evaluate nodules sub-work step may permit a user zoom in and out of the nodule image and/or cancel the volume of interest. The identify calcifications sub-work step may generate a histogram to identify calcifications in the nodule.

Figure 12:
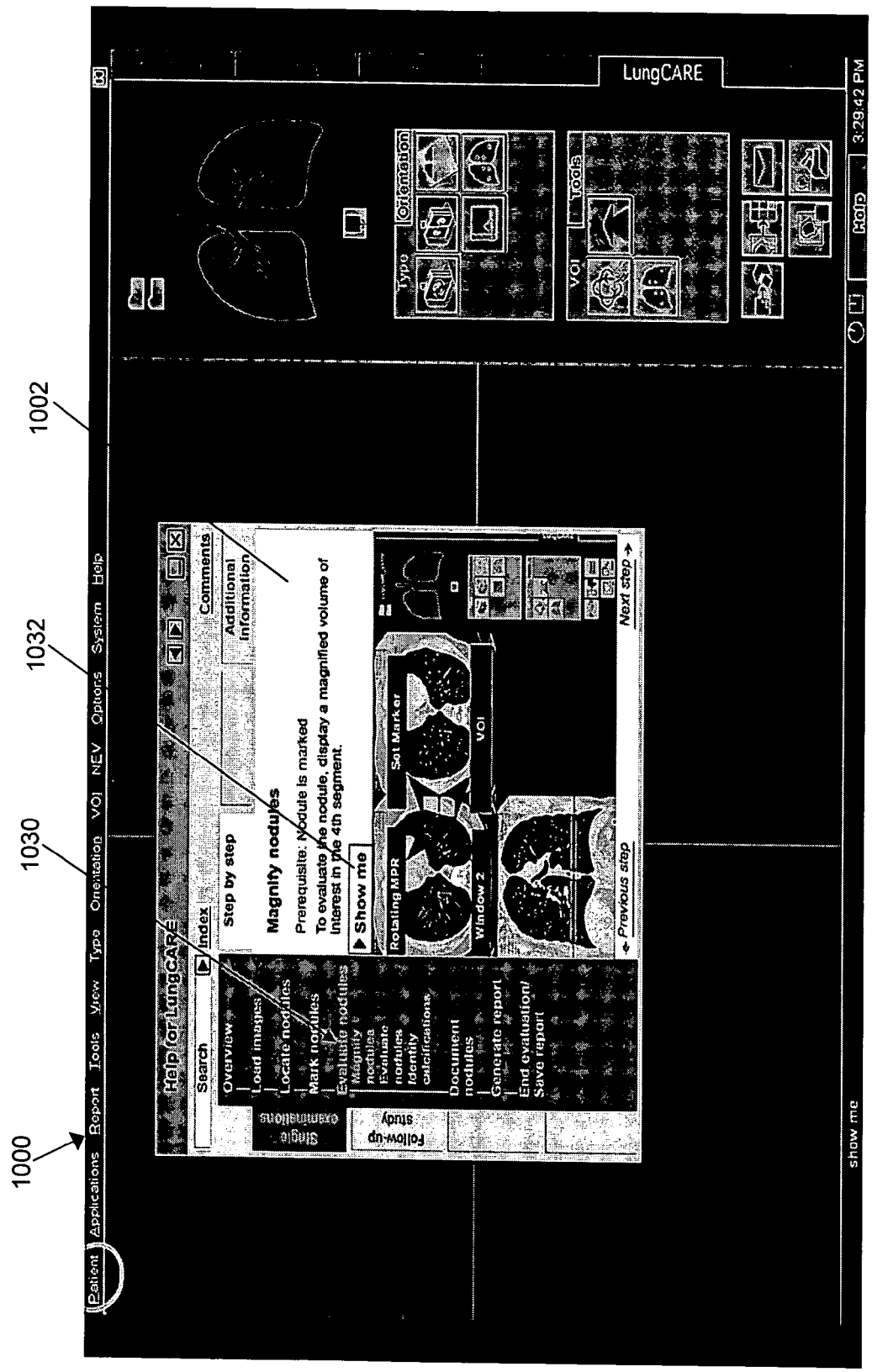
FIG. 12 illustrates another exemplary workflow assistance for a workflow assisted by a user interface according to one embodiment.
Figure 13:
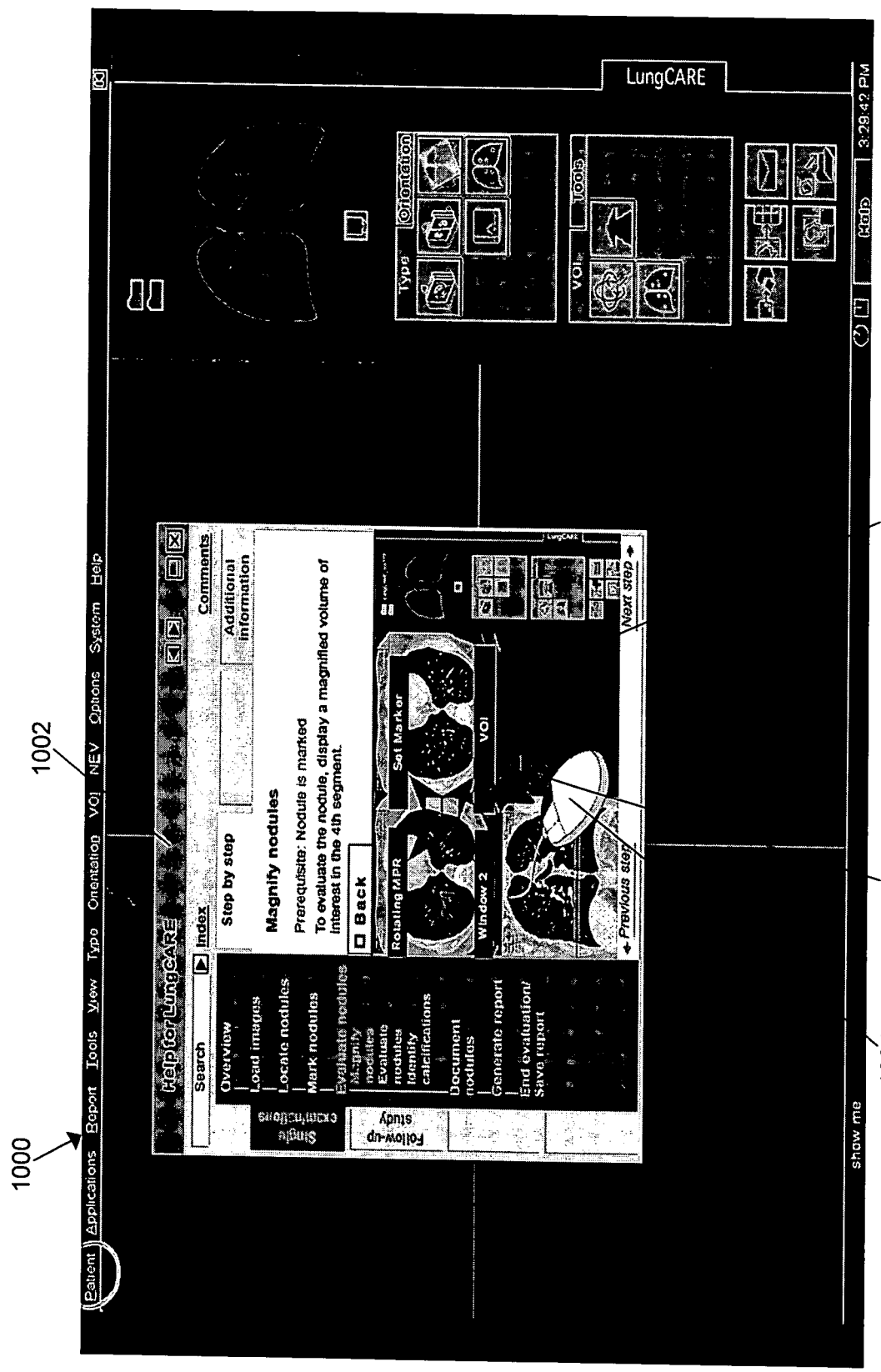
FIG. 13 illustrates another exemplary workflow assistance for a workflow assisted by a user interface according to one embodiment.

FIGS. 12 and 13 illustrate workflow assistance associated with the magnify nodules 1030 sub-work step of the exemplary workflow. Workflow assistance 1002 in the form of step by step textual instructions detailing the proper operation of the user interface are initially displayed after a user requests workflow assistance. Subsequently, if the user is not satisfied with the level of direction provided by the textual instructions, the user may access a virtual simulation demonstrating the proper operation of the user interface by performing an operation on the "show me" button 1032.

In the example shown in FIG. 13, an operation performed on the "show me" button 1032 results in a virtual simulation 1010 that is an animation being displayed on the user interface. The virtual simulation 1010 shows the user how to operate an input device, a mouse in this case, to properly operate the user interface to complete the magnify nodules 1030 sub-work step. In the animation, an animated mouse 1034 is moved across the user interface 1000. An animated arrow 1036 provides further guidance to the user regarding how to properly perform the work step or sub-work step. Alternate guidance may be provided.

Figure 14:
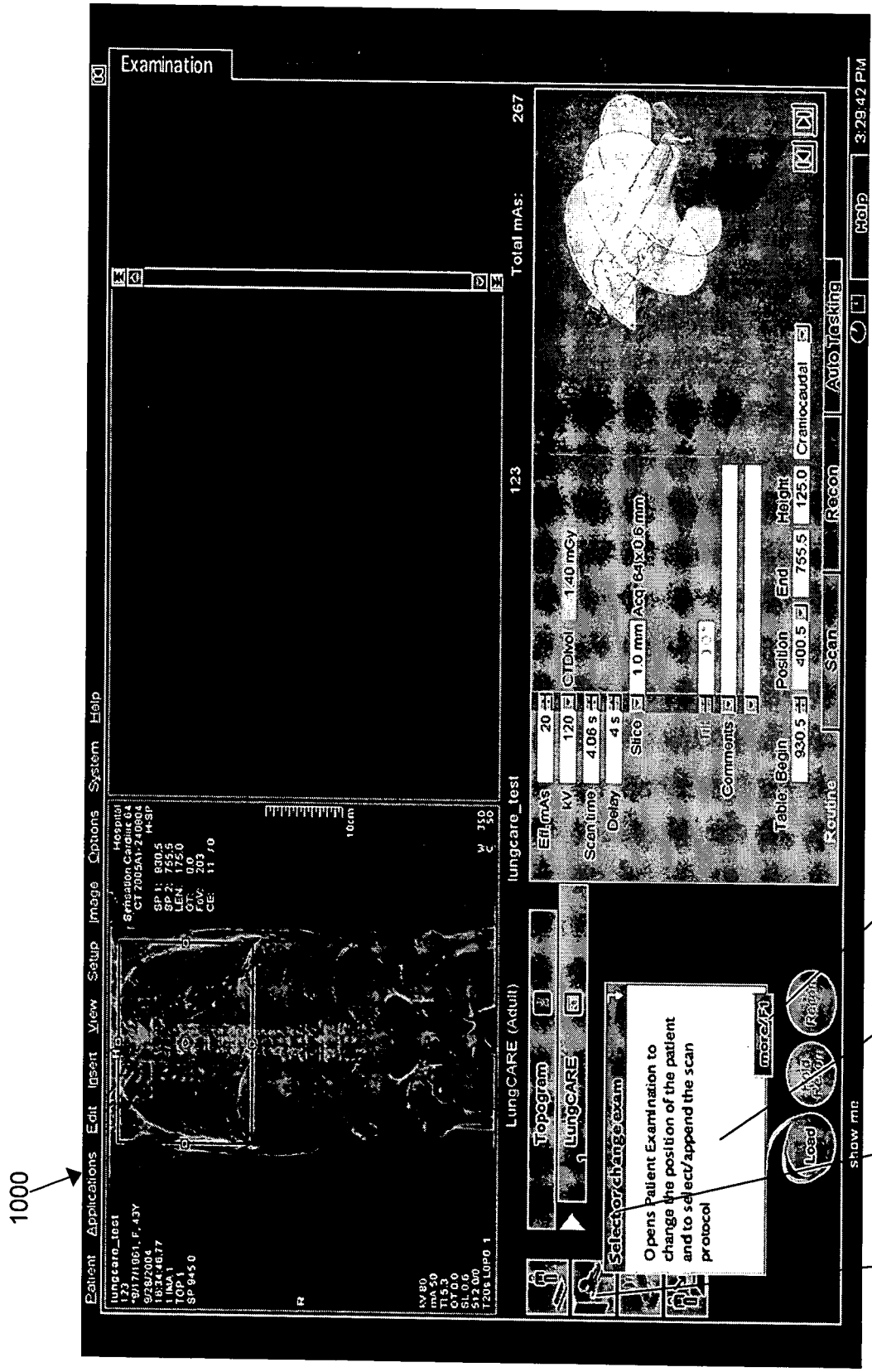
FIG. 14 illustrates an exemplary manner of accessing workflow assistance according to one embodiment.

FIG. 14 illustrates an exemplary manner of accessing workflow assistance from the user interface. The user interface displays a number of icons 1020 corresponding to a specific work step. As discussed above, by performing a primary operation on the icon 1020, the work step may be initiated. By performing a secondary operation on the icon 1020, a functional identifier 1040 may be displayed. In the example shown, the functional identifier 1040 identifies the work step as the "select or change exam" work step.

Subsequently, if a user desires more information regarding the function of the work step after reading the functional identifier 1040, a third operation may be performed on the functional identifier 1040 to display a functional explanation 1042. The functional explanation 1042 shown explains that the function of the "select or change exam" work step is "opens patient examination to change the position of the patient and to select/append the scan protocol." The functional explanation 1042 in the example illustrated is displayed in a pop-up window having an associated "more" button 1044.

After reading the functional explanation 1042, a user may determine that workflow assistance regarding the "select or change exam" work step is desired. A fourth operation performed on the "more" button 1004 will display workflow assistance regarding the "select or change exam" work step. Accordingly, work flow assistance is accessed via a secondary operation performed on a icon associated with the work step. Alternate manners of accessing workflow assistance may be user.

For the exemplary medical procedure shown, the workflow assistance may train a user on how to cancel a volume of interest (VOI), zoom in or out, rotate a nodule or other region of interest, or evaluate the nodule. The user interface may present an error management message indicating an error has occurred in the performance in the current work step. For instance, the error management message may include information related to the evaluate nodules sub-work step. The message may indicate that the evaluation of the nodule is not possible due to the mouse not being centered in the nodule. The user interface may present information regarding corrective action to properly perform the work step, such as centering the mouse in the nodule and restarting the work step.

Another error management message of the exemplary medical procedure indicates that the evaluation of the nodule is not possible because the marked nodule is not in the slice plane. The user interface presents information regarding corrective action to properly perform the work step, which in this case is to change the type of display and optimize the position of the marker by clearing the previous marker and centering a new marker in the nodule. Additional, fewer, or alternate error management messages may be used.

As noted above, the exemplary workflow may include the document nodules, the generate report, and the end evaluation/save report work steps. The document nodules work step permits a user to enter and save nodule locations and details. The generate report work step permits a user to generate a patient specific report. The end evaluation/save report work step may permit a user to save the currently completed workflow as a report for subsequent retrieval.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

What is claimed is:

1. A computer-based interactive user-interface training system providing workflow assistance and simulating user-interface operation, the system comprising:
   a data processor operable to assist a performance of a workflow, the workflow having a plurality of pre-determined work steps to be performed sequentially, the data processor being configured to track a user's progress through the plurality of predetermined works steps and identify a current work step from among the plurality of predetermined work steps; and
   a user interface generated by the data processor and operable to (1) initiate the current work step in the workflow, and (2) alternatively, respond to queries for information regarding a current work step and provide workflow assistance associated with a performance of the current work step via a display screen, the workflow assistance including at least step by step instructions detailing to the user a proper performance of the current work step, based on a previous operation of the current work step, to guide completion of the current work step, the user interface configured to individually display, on the display screen, each step by step instruction explaining to the user the proper performance of the current work step to complete the current work step, the workflow assistance further including a virtual simulation to be presented on the display screen demonstrating to the user the proper performance of the current work step to complete the current work step,
   wherein, as the plurality of pre-determined work steps within the workflow are being performed sequentially, when the user has questions regarding the proper performance of the current work step, upon receipt of the request for information regarding the current work step, the user interface presents on the display screen the workflow assistance that details or demonstrates the proper performance of the current work step required to properly complete the current work step such that the workflow is recommenced and the current work step is completed by the user based on the previous operation of the current work step as detailed by at least one of the step by step instructions or demonstrated by the virtual simulation that simulates realistic operation of the user interface via the display screen, and
   wherein the workflow assistance includes step by step instructions relate to a proper performance of a previous work step and a next work step from among the plurality of pre-determined work steps, the instructions based on a previous operation of the previous work step and the next work step.

2. The system of claim 1, wherein the workflow assistance includes alternate step by step instructions and an alternate virtual simulation illustrating an alternate proper performance of the current work step, based on an alternate previous operation of the current work step, to complete the current work step.

3. The system of claim 1, wherein the workflow involves analysis of images obtained from a medical imaging process and the user interface displays the images to facilitate the evaluation of a region of interest.

4. The system of claim 1, wherein the data processor is operable to identify an error in the operation of the user interface and the user interface is operable to display an associated error message and recommended remedial actions.

5. The system of claim 1, wherein the user interface is operable to enter and save user entered comments at every work step in the workflow.

6. The system of claim 1, wherein the user interface is operable to present workflow assistance that is accessible from a help menu superimposed over other images displayed on the user interface such that the other images remain visible.

7. The system of claim 1, wherein the user interface is operable to present workflow assistance that is indirectly accessible from an icon associated with a work step.

8. The system of claim 1, wherein the workflow assistance detailing the proper performance of the current work step to complete the current work step is both accessible via a single operation on a global icon on the user interface and via an operation on an icon dedicated to the current work step.

9. The system of claim 1, wherein the virtual simulation demonstrating the proper performance of the current work step to complete the current work step visually demonstrates the proper operation of a mouse during the previous operation of the current work step to properly complete the current work step.

10. The system of claim 1, wherein the virtual simulation demonstrating the proper performance of the current work step to complete the current work step is an animation that visually demonstrates the proper operation of an input device during the previous operation of the current work step to properly complete the current work step.

11. A computer-based interactive user-interface training system providing workflow assistance and simulating user-interface operation, the system comprising:
   a data processor operable to assist a current workflow, the current workflow having a plurality of pre-determined work steps to be performed sequentially by a user controlling an interactive software application via the data processor;
   a user interface displayed on a display screen and coupled with the data processor, the user interface operable to initiate a current work step in the current workflow and alternatively provide workflow assistance associated with a performance of the current work step, the workflow assistance including textual instructions and visual simulation related to a previously performed proper operation of the user interface in a previous workflow and provided to the user in the course of the performance of the current work step in the current workflow, the textual instructions comprising a message explaining action to be taken by a user and the visual simulation simulating a proper operation of an input device such that by following the textual instructions and by mimicking guidance provided by the virtual simulation, the user may properly complete the current work step in the current workflow; and the user interface configured to display on the display screen the textual instructions and visual simulation workflow assistance detailing the previously performed proper operation of the user interface during the course of the performance of the current work step such that the user interface is operable in accordance with the textual instructions or visual simulation displayed on the display screen to properly complete the current work step in the current workflow.

wherein the workflow assistance includes step by step instructions related to a proper performance of a previous work step and a next work step from among the plurality of pre-determined work steps, the instructions based on a previous operation of the previous work step and the next work step.

\* \* \* \* \*